United States Patent
Tsibris et al.

(10) Patent No.: US 6,218,594 B1
(45) Date of Patent: Apr. 17, 2001

(54) GUINEA PIG MODEL FOR LEIOMYOMAS

(75) Inventors: John C. M. Tsibris, Valrico; Kathy B. Porter, Apollo Beach, both of FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/068,365

(22) PCT Filed: Nov. 8, 1996

(86) PCT No.: PCT/US96/17969

§ 371 Date: Sep. 16, 1998

§ 102(e) Date: Sep. 16, 1998

(87) PCT Pub. No.: WO97/17091

PCT Pub. Date: May 15, 1997

Related U.S. Application Data (60) Provisional application No. 60/006,377, filed on Nov. 8, 1995.

(51) Int. Cl.⁷ ................................................. A01K 67/00
(52) U.S. Cl. ......................... 800/3; 800/9; 800/8; 800/21
(58) Field of Search ................................ 800/3, 8, 9, 13, 800/14, 21

(56) References Cited

U.S. PATENT DOCUMENTS

| | | |
|---|---|---|
| 4,439,196 | 3/1984 | Higuchi . |
| 4,447,224 | 5/1984 | DeCant, Jr. et al. . |
| 4,447,233 | 5/1984 | Mayfield . |
| 4,475,196 | 10/1984 | La Zor . |
| 4,486,194 | 12/1984 | Ferrara . |
| 4,487,603 | 12/1984 | Harris . |
| 4,925,678 | 5/1990 | Ranney . |
| 4,959,217 | 9/1990 | Sanders et al. . |
| 5,167,616 | 12/1992 | Haak et al. . |
| 5,169,383 | 12/1992 | Gyory et al. . |
| 5,225,182 | 7/1993 | Sharma . |
| 5,622,974 * | 4/1997 | Muehl ................................. 514/320 |
| 5,643,896 * | 7/1997 | Cullinan et al. ...................... 514/146 |

OTHER PUBLICATIONS

Cremona, O. et al. Differential Protein Expression in Aortic Smooth Muscle Cells Cultured from Newborn and Aged Rats. Experimental Cell Research 217(2):280–287, 1995.*

Porter, K.B. et al. Estrogen–Induced Guinea Pig Model for Uterine Leiomyomas: Do the Ovaries Protect? Biology of Reproduction 52:824–832, 1995.*

Kumar, V. et al. Basic Pathology, Fifth Edition. W.B. Saunders Company, Philadelphia, 1992.*

Allegretto et al., "Transactivation properties of retinoic acid and retinoid receptors in mammalian cells and yeast. Correlation with hormone binding and effects of metabolism" J Biol Chem 268:26625–26633 (1993).

Barbieri, ed. Leiomyoma utero in Seminars in reproductive endocrinology 10:301–390 (1992).

Batra, et al., "Sex steroids in plasma and reproductive tissues of the female guinea pig" Biol. Reprod. 22:430–437 (1980).

Breslow, "Mouse models of atherosclerosis" Science 272:685–688, 1996.

Bulun et al., "Expression of the CYP19 gene and its product aromatase cytochrome P450 in human uterine leiomyoma tissues and cells in culture" J Clin Endocrinol & Metab, 78:736–743 (1994).

Carlson et al., "Indications for hysterectomy" New Engl J Med, 328:856–860 (1993).

Enzinger et al., in Soft Tissue Tumors, 2nd ed., St. Louis: Mosby, p. 89 (1988).

Everitt et al., "Rodent model of reproductive tract leiomyomata. Clinical and pathology features" Amer J Pathol 146:1556–1567 (1995).

Fekete, "Animal models in experimental atherosclerosis: a critical review" Acta Veterinaria Hungarica 41:3–9 (1993).

Ferenzy and Richart, in Female reproductive system: dynamics of scan and transmission electron microscopy, New York: Wiley and Sons, pp. 197–207 (1974).

Field et al., "Spontaneous reproductive tract leiomyomas in aged guinea–pigs" J Comp Pathol, 101:287–294 (1989).

Finkelman et al., "Ovariectomy selectively reduces the concentration of transforming growth factor ( in rat bone: implications for estrogen deficiency–associated bone loss" Proc Natl Acad Sci USA, 89:12190–12193 (1992).

Fotsis et al., "The endogenous oestrogen metabolite 2–methoxyoestradiol inhibits angiogenesis and suppresses tumor growth" Nature, 268:237–239 (1994).

Friedman and Barbieri: "Leuprolide acetate". Applications in gynecology. Curr Probl Obstet Gynecol Fertil 11:205 (1988).

Fujii et al., "Progesterone–induced smooth muscle–like cells in the subperitoneal nodules produced by estrogen. Experimental approach to leiomyomatosis peritonealis disseminata". Am J Obstet Gynecol 139:164–172 (1981).

Furukawa et al., J. Biol. Chem. 267:17121–17127 (1992).

Glutek and Hobkirk, "Estrogen sulfatase and steroid sulfatase activities in intrauterine tissues of the pregnant guinea pig" J Steroid Biochem Mol Biol, 37:707–715 (1990).

Harkness and Wagner, in The Biology of Rabbits and Rodents, 3rd ed. Philadelphia: Lea Sebiger Publisher; p. 21 (1989).

(List continued on next page.)

Primary Examiner—John L. LeGuyader
Assistant Examiner—Michael C. Wilson
(74) Attorney, Agent, or Firm—Kohn & Associates

(57) ABSTRACT

A method of making a model test system in guinea pigs for leiomyomas and early stage atherosclerosis by ovariectomizing young female guinea pigs, and co-implanting a continuous slow release device for releasing an estrogenic compound or analog thereof and a retinoid compound or analogs thereof.

6 Claims, 2 Drawing Sheets

OTHER PUBLICATIONS

Henderson et al., in Ultrastructural appearance of tumours, 2nd ed., Edinburgh: Churchill Livingstone, p. 231–238 (1986).

Howe et al., "Rodent model of reproductive tract leiomyomata. Establishment and characterization of tumor–derived cell lines" Amer J Pathol 146:1568–1579 (1995).

Hsu et al., "The use of avidin–biotin–peroxidase techniques" J Histochem Cytochem, 29:577–580 (1981).

Kiechle–Schwarz et al., Nonrandom cytogenetic changes in leiomyomas of the female genitourinary tract. A report of 35 cases. Cancer Genet Cytogenet 53:125 (1991).

Kjerulff et al., Hysterectomy and race. Obstet Gynecol 82:757–764 (1993).

Kojima et al., "In vivo isomerization of retinoic acids. Rapid isomer exchange and gene expression" J Biol Chem 269:327000 (1994).

Lanari et al., "Progesterone receptors in estrogen–induced fibromatosis of guinea pigs" Cancer Lett, 51:235–245 (1990).

Larner et al., "The isolation and characterization of estradiol–fatty acid esters in human ovarian follicular fluid" J Biol Chem, 268:13893–13899 (1993).

Lipschutz, "Experimental fibroids and the antifibromatogenic action of steroid hormones" J Am Med Assoc, 120:171–175 (1942).

Lipschutz and Vargas, "Experimental tumorigenesis with subcutaneous tablets of oestradiol" Lancet, 236:1313–1318 (1939).

Lipschutz and Vargas, "Structure and origin of uterine and extragenital fibroids induced experimentally in the guinea pig by prolonged administration of estrogens" Cancer Res 1:236–249 (1941).

Lipschutz et al., "Antitumorigenic action of progesterone" Lancet 1:420–421 (1939).

Lumsden, et al., "The binding of steroids to myometrium and leiomyomata (fibroids) in women treated with the gonadotrophin–releasing hormone agonist Zoladex (ICI 118630)" J Endocrinol 121:389 (1989).

Luna, in *Manual of Histologic Staining Methods of the Armed Forces* Institute of Pathology, 3rd ed., New York:McGraw–Hill, 38–39 and 94 (1968).

Mangelsdorf and Evans, "The RXR heterodimers and orphan receptors" Cell;83:841–850 (1995).

Mangelsdorf et al., "Overview: The nuclear receptor superfamily: The second decade" Cell 83:835–839 (1995).

Nagpal et al., "Separation of transactivation and AP1 antagonism functions of retinoic acid receptor" J Biol Chem 270:923 (1995).

Nelson, "Endometrial and myometrial changes, including fibromyomatous nodules, induced in the uterus of the guinea pig by the prolonged administration of oestrogenic hormone" Anat Rec, 68:99–102 (1937).

Nicosia et al., "Isolation and ultrastructure of rabbit ovarian mesothelium (surface epithelium)" Int J Gynecol Pathol, 3:348–360 (1984).

Paigen et al., "The mouse as a model for human cardiovascular disease and hyperlipedimia" Current Opinion in Lipidology 5:258–264, 1994.

Pandis et al., "High resolution mapping of considtent leiomyoma breakpoints in chromosomes 12 and 14 to 12q15 and 14q24.1" Genes Chrom Cancer 2:227 (1990).

Porter et al., Ovariectomized guinea pigs with silastic 17$–estradiol implants: How good a model for leiomyomas? Biol Reprod, 48(suppl 1):89 (abstract 124) (1993).

Porter et al., "Estrogen–induced guinea pig model for leiomyomas: Do the ovaries protect?" Biol. Reprod. 52:824–832 (1995).

Porter et al., "Raloxifene Causes Rapid Regression of Abdominal Wall Leiomyomas in the Estrogen–Induced Guinea Pig Model" *J Soc Gynecol Invest,* vol. 3, No. 2 (Supplement) (1996).

Rein et al., "Cytogenetic abnormalities in uterine leiomyomata" Obstet Gynecol 77:923–926 (1991).

Rein and Nowak, "Biology of uterine myomas and myometrium in vivo" Semin Reprod Endocrinol, 10:310–319 (1992).

Rogers and Blumenthal, "Studies of guinea pig tumors. I. Report of 14 guines pig tumors, with a review of the literature" Cancer Res, 20:191–197 (1960).

Romagnolo et al., "Estradiol–dependent uterine leiomyomas in transgenic mice" J Clin Invest 98:777–784 (1996).

Sadan et al., "Oestrogen and progesterone receptor concentration in leiomyoma and normal myometrium" Ann Clin Biochem 24:263 (1987).

Savouret et al., "Interplay between estrogens, progestins, retinoic acid and AP–1 on a single regulatory site in the progesterone receptor gene" J Biol Chem 269:28955 (1994).

Schoen, "Blood Vessels", In Pathologic basis of disease, R.S. Cotran, V. Kumar and S.L. Robbins (editors), 5th ed., W.B. Saunders Co., Philadelphia, PA., 1994, pp. 467–516.

Schurch et al., in Sternberg SS (ed.), Histology for Pathologists. New York: Raven Press, pp. 109–144 (1996).

Senekjian et al., "Comparison of the quantity of estrogen receptors in human endometrium and myometrium by steroid–binding assay and enzyme immunoassay based on monoclonal antibodies to human estrophilin" Am J Obstet Gynecol 160:592 (1989).

Simionescu and Simionescu, "Preatherosclerotic events: pathoiochemical changes occuring in the arterial wall before monocyte migration" FASEB J 7:1359–1366 (1993).

Stewart and Friedman, "Steroidal treatment of myomas: preoperative and long–term medical therapy" Semin Reprod Endocrinol, 10:344–357 (1992).

Tsibris and Spellacy, "Potential regulation of uterine leiomyomas by epidermal growth factor, platelet–derived growth factor, IGF–I, insulin and steroids", In The Extracellular Matrix and the Reproductive Tract, PC Leppert and JF Woessner Jr, eds, Perinatology Press, Ithaca NY, pp 224–234 (1991).

Tsibris et al., "Estrogens and protein disulfide isomerase systems", In The New Biology of Steroid Hormones. R.B. Hochberg, and F. Naftolin, editors. Serono Symposia vol. 74, Raven Press, NY. 235–249 (1991a).

Wilcox et al., "Hysterectomy in the United States, 1988–1990" Obstet Gynecol., 83:549–555 (1994).

Yang et al., "Effects of long–term estradiol exposure on the hypothalamic neuron number" Acta Endocrinol, 129: 543–547 (1993).

\* cited by examiner

GUINEA PIG MODEL FOR LEIOMYOMAS

CROSS REFERENCE TO RELATED APPLICATIONS

The present application is a national phase filing of PCT Application Ser. No. PCT/US96/17969 filed Nov. 8, 1996, now Publication Number WO97/17091, which claims priority to Provisional Application No. 60/006,377 filed Nov. 8, 1995, both of which are incorporated herein by reference.

BACKGROUND OF THE INVENTION

1. Technical Field

The present invention relates to the development of a model test system for studying leiomyomas and atherosclerosis treatment modalities of leiomyomas and atherosclerosis.

2. Background Art

Uterine leiomyomas: Leiomyomas (fibroids) are the most common pelvic benign clonal tumors of the uterus originating from myometrial smooth muscle cells (reviews by Barbieri, 1992 and references therein; Tsibris and Spellacy, 1991) that may cause bleeding, a mass, or pelvic pressure (Barbieri and Speroff, 1992). They occur in 25% of women over 35, are a major (30%) cause of hysterectomy. They occur in 20–30% of women over 30 and are therefore an important issue in pregnancy as many women delay childbearing to their late thirties. Leiomyomas are found more frequently in African American than caucasian women (Kjerulff et al, 1993).

Leiomyomas are clonal tumors believed to originate from single myometrial cells (Barbieri and Speroff, 1992; Tsibris and Spellacy, 1991; Rein and Nowak, 1992). They are discrete encapsulated tumors, found submucosally (beneath the endometrium), intramurally (within the myometrium) and subserosally (projecting out of the serosal compartment of the uterus). Some leiomyomas become partially calcified. Although their etiology is unknown it is believed that estrogens, and perhaps progesterone, regulate their development and growth because leiomyomas increase in size during reproductive life and regress after menopause. Estradiol-17β ($E_2$) and progesterone ($P_4$) have been implicated in their development and growth. Therapy with agonists (for example Leupron) of gonadotropin releasing hormone (GnRH), which inhibit gonadal function and decrease serum $E_2$, results in a 40–60% decrease in leiomyoma size that is reversed when therapy is discontinued (Stewart and Friedman, 1992). It should be noted that Leupron therapy cannot be undertaken for longer than six months due to the risk of osteoporosis.

Karyotypic translocations, rearrangements, breakpoints, mainly in chromosomes 6p, 7q21-31, 12q13-15 and 14q23-24 occur in 20–50% of leiomyomas and bear similarity to those found in lipomas and meningiomas (Kiechle-Schwarz et al, 1991; Pandis et al, 1990; Rein et al, 1991) Leiomyomas have significantly higher levels of $E_2$ receptors ($E_2R$) and $P_4$ receptors ($P_4R$) than normal myometrium throughout the menstrual cycle (Lumsden et al, 1989; Sadan et al, 1987). Therapy with GnRH agonists (GnRHa), which inhibit gonadal function and decrease serum $E_2$ below 20 pg/ml, result in a 40–60% decrease in the size of leiomyomas (Friedman and Barbieri, 1988). Paradoxically, leiomyomas removed after 3 months of GnRHa therapy had lower $E_2$ but increased $E_2R$, compared to untreated leiomyomas, as determined by both [$^3H$]-$E_2$ displacement assays and immunoassays using monoclonal $E_2R$ antibodies (Lumsden et al, 1989; Senekjian et al, 1989).

A leiomyoma animal model is needed that resembles, as closely as possible, human uterine leiomyomas. This model would be valuable in unraveling the molecular mechanism(s) by which leiomyomas are regulated in vivo. More importantly, the model would facilitate the design and testing of new therapeutic modalities aimed at retarding leiomyoma growth or even preventing their formation.

Nelson (1937) and Lipschutz and associates (1938; 1939, 1941, 1942) produced tumors on the uterine serosa and the abdominal cavity of guinea pigs after three months exposure to various estrogens. The tumors did not develop if the estrogen treatment was halted, interrupted for a week, or combined with high doses of $P_4$.

Female guinea pigs are more susceptible to tumors than males (Rogers and Blumenthal, 1960). Spontaneous uterine leiomyomas occur in 8.4% of older guinea pigs with a mean age of four years, the 80% percentile of their life span (Field et al., 1989; Harkness and Wagner, 1989). In 1981, Fujii et al., (1981) injected $E_2$ benzoate intramuscularly three times a week, but electron microscopy revealed that the nodules produced after three months of treatment were composed of only fibroblasts. Only when the injections with estrogen continued for a month and were supplemented with weekly injections of 1 mg $P_4$ did the investigators find nodules composed of cells resembling smooth muscle and decidua cells (Fujii et al., 1981); if a higher dose (3 mg) of $P_4$ was used, no nodules were formed.

Applicants have previously improved the Lipschutz guinea pig model by exposing animals continuously via a slow release system to pregnancy level serum $E_2$ (Porter, et al, 1993). These guinea pigs developed leiomyomas mainly on the uterine subserosa and in the anterior abdominal wall. After nine months, numerous abdominal tumors appeared resembling leiomyomatosis peritonealis disseminata which is a very rare disease in humans. However, this model does not provide as close a correlation with the human disease as needed, in particular the appearance of intra-abdominal wall tumors is not seen in humans.

Everitt et al. (1995) and Howe et al. (1995) report that small uterine leiomyomas and leiomyosarcomas were spontaneously formed in Eker rats, as part of a familial renal cancer syndrome, a result of a germline mutation in the tuberous sclerosis gene. It appears that these uterine tumors are similar to the small serosal leiomyomas applicants observed in the E2-only-treated guinea pigs (prior art model). As seen in applicants' prior model numerous small (1–2 mm) or larger cysts located along the blood supply of the horn were seen in the Eker rat tumors. This model again does closely resemble the human leiomyomas as well as being associated with a mutant gene and cancer syndrome which are not seen in the human condition.

Very recently, a transgenic mouse model for uterine leiomyomas was reported by Romagnolo et al. (1996). The formation of leiomyomas in this model still depends on the administration of estrogens. However, preparing and maintaining transgenic animals is expensive and labor intensive. It would be useful to have a model that did not require transgenic manipulations. Also a mouse model does not easily allow for laparoscopic techniques because of the small size of the animal.

There are many animal models for atherosclerosis, from primates, pigs, rabbits to mice, the latter being highly resistant to the disease (Breslow, 1996; the May 3, 1996 issue of Science is devoted to Cardiovascular Medicine). Most, if not all animals, can develop atherosclerosis by dietary manipulation, usually, a high fat diet to induce hypercholesterolemia (Fekete, 1993), by genetic manipulation [transgenic and knockout mice] (Paigen et al., 1994) or exposure to a virus. However, these models do not allow for clarifying yet unexplored mechanisms of pre-atherosclerotic events (Simionescu and Simionescu, 1993) with emphasis on proliferation of vascular smooth muscle cells that become the dominant cell types (Moraghan et al., 1996). It would be useful to have a model where therapy for early pre-atherosclerotic events can be explored.

SUMMARY OF THE INVENTION

According to the present invention, a model test system in guinea pigs for studying leiomyomas and early stage atherosclerosis is disclosed. The model includes ovariectomized young female guinea pigs co-implanted with a continuous slow release device in a preferred embodiment for releasing an estrogenic compound or analogues thereof and for a retinoid compound or analogues thereof. The model test system allows for the testing of pharmaceutical compounds for the treatment of leiomyomas and for atherosclerosis.

The present invention also provides a method of monitoring the effectiveness of the pharmaceutical agent being used to shrink leiomyoma without waiting for the endpoint of tumor shrinkage. The present invention further provides a method of treatment of leiomyomas by treating with antagonists or agonists of the family of nuclear retinoic acid receptors.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 2A–B are photographs of immunoblots of human (A) and guinea pig (B) uterine extracts stained with a polyclonal antibody to peroxisome proliferation activated receptor (PPAR subtype gamma2), wherein on the left vertical axis the molecular weight markers indicated with PPAR bands are at 64 and 58 KDa and wherein in FIG. 2A, the lanes are as follows: (A) is Myometrium of FS, (B) is Leiomyoma of FS, (C) is Myometrium of MH2, (D) is Leiomyoma of MH2, (E) is Myometrium of SLC, (F) is Leiomyoma of SLC, (G) is Myometrium of JB, and (H) is Leiomyoma of JB, and wherein in FIG. 2B, the lanes are as follows: (1) is Uterine horn of GP1, (2) is Serosal leiomyoma of GP1, (3) is Uterine horn of GP2, (4) is Serosal leiomyoma of GP2, (5) is Abdominal wall leiomyoma of GP2, (6) is Uterine horn of GP3, (7) Serosal leiomyoma of GP3, and (8) Abdominal wall leiomyoma of GP3.

DETAILED DESCRIPTION OF THE INVENTION

The present invention provides a small animal model that is helpful in unraveling molecular mechanisms that regulate leiomyomas (fibroids) in vivo and initiation of atherosclerosis (early stage) and in the design and testing of new therapeutic approaches to prevent or control leiomyoma growth and initiation of atherosclerosis. The present invention provides the method of making a model test system in guinea pigs for leiomyomas by ovariectomizing young female guinea pigs, by continuously treating with estrogenic and retinoid compounds and their analogues. In a preferred embodiment a continuous slow release means is implanted for releasing the compound. Alternatively, oral or intraperitoneal delivery can be used.

Applicants determined that it would be useful to improve the existing guinea pig model for leiomyoma (Nelson, 1992; Lipschutz and Iglesias, 1938; Lipschutz and Vargas, 1939; Lipschutz and Vargas, 1941; Lipschutz, 1942) by increasing its similarities to human uterine leiomyomas. Applicants initially determined (Porter et al, 1993, 1995) that continuous slow release of estradiol-17β ($E_2$) was required for the production of leiomyoma in ovariectomized guinea pigs as set forth in Example 1 herein below, but this model produced in addition to small uterine leiomyoma, abdominal wall tumors. Applicants then developed the present inventive new model in which ovariectomized guinea pigs were exposed for at least one month to estrogenic compound implants and implants containing a retinoid compound as shown in Example 2 and in which there are essentially no abdominal wall tumors.

It was unexpected to find that the model also leads to intimal thickening of the aorta (FIG. 1) which is an early stage of atherosclerosis. Intimal thickening consists of proliferating smooth muscle cells and fibroelastic tissue. Smooth muscle cells are an important element of vascular reparative processes and of proliferative diseases including preatherosclerotic lesions (Schoen, 1994). This observation was particularly unexpected in that it is widely reported that estrogens exert a protective effect on the cardiovascular system.

The novel model test system (Example 2) in guinea pigs for leiomyomas includes ovariectomized young guinea pigs co-implanted with a continuous slow release means for at least one month for releasing an estrogenic compound or analogues thereof and with a retinoid compound or analogues thereof. In a preferred embodiment, estradiol-17β ($E_2$) and retinoic acid (RA) or analogues thereof are used. Young guinea pigs are defined are less than one year old and under 900 grams in weight.

In the preferred embodiment the continuous slow release means can be any means that releases the drugs slowly and continuously such as Alza® pumps or for example the same means that are used by Norplant®. Pellets can be used if they do not become encapsulated so that release is impeded. In a preferred embodiment, silastic implants are used. These implants are 3×30 mm and made with Dow Corning Co. (Midland, Mich.) medical grade silastic tubing (no. 602-305) and adhesive silicone (type A, no. 891) sealant (Porter et al, 1995). The area of the implant, not the amount of substance is the main determinant of the amount of compound delivered to the subject.

In general, the continuous slow release means of the present invention can be administered parenterally to the guinea pig in the form of slow-release subcutaneous implants or targeted delivery systems such as monoclonal antibodies, vectored delivery, iontophoretic, polymer matrices, liposomes, and microspheres which are known in the art and have been developed for mammalian use. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. Alternatively, oral or intraperitoneal delivery can be used.

Dosage of the administered compounds must be regulated so that the retinoic acid or retinoic-acid-analogue/derivative is not toxic, i.e. no liver damage. Slow-release in this regard is useful since no high bolus amounts are delivered. Appropriate screening for liver activity can be used to monitor for toxicity. In addition younger female guinea pigs must be used since the retinoic acid dosages have been observed in the three older OVX animals tested to be toxic.

In one embodiment the $E_2$ implant contains approximately 50–60 mg $E_2$ powder. The retinoic acid silastic implant contains approximately 40 mg of retinoic acid (RA). To produce large tumors in a short period of time two $E_2$ implants are used for each retinoic acid implant. To lower the $E_2$ burden on the liver and prevent RA liver toxicity it is possible to implant only one $E_2$ implant and one RA implant. Tumors produced with this protocol are smaller and take longer to form. Half-length implants of the same diameter silastic tubing ("mini-implants") can also be used; again tumors are smaller and take longer to form.

In general, the estrogenic compound can be estradiol-17β ($E_2$), $E_2$-metabolites, estrone, 17-esters of $E_2$, 2-methoxyestradiol, catecholestrogens and synthetic estrogens such as diethylstilberestrol as used by Lanari et al, 1990. The analogues can be different forms of estradiol-17β ($E_2$), $E_2$-metabolites and estrone that are functionally equivalent. Compounds that are metabolized to these compounds when administered are also considered analogues. In general estradiol analogues are free phenolic compounds or phenol derivatives (esters, ethers) which in the body are metabolized to free phenols.

Retinoids are derivatives of vitamin A and modulate cellular proliferation and differentiation. This action is exerted through nuclear retinoid receptors (reviews by Mangelsdorf, et al., 1995) which are members of the nuclear receptor superfamily. The retinoid receptors are divided in two subfamilies, the retinoic acid receptors (RAR), which bind all-trans (atRA) and 9-cisRA, and the retinoid X receptors (RXR) which bind 9-cisRA. Each group of RAR and RXR is encoded by three different genes (α, β, γ) and each subtype differs in their amino terminus due to alternate mRNA splicing and different promoters. The classification between the RAR and RXR subfamilies of retinoid receptors is based on their, 1) primary sequence differences, 2) binding affinity to synthetic and naturally occurring retinoids, and 3) differential regulation of target genes (Allegreto et al., 1993). The complexity of retinoid receptor regulation of gene expression is further complicated by the fact that RXRs can form heterodimers with RAR, PPAR, vitamin D receptor (VDR) and thyroid receptor (TR) subtypes (Mangelsdorf and Evans, 1995) in order to recognize hormone response elements located in their target genes. There is functional redundancy between the three RAR types but it varies with the nature of the RA target gene.

An alternative indirect pathway exists where RARs interact with the AP-1 components (c-Fos and c-Jun) resulting in inhibition of AP-1 activity without binding to DNA at specific response elements (Savouret et al., 1994). AP1 regulates expression of metalloproteases, cytokines and other factors that control turnover of the extracellular matrix (Nagpal et al., 1995), and are of potential interest in the study of fibrotic reactions.

Metabolites of retinoid compounds that give rise to retinoic acid (RA) or retinoic-acid-analogues which have the same functional activity are used for induction of the model. Oxidative metabolites that give rise to aldehyde or acid forms are preferred. For example, either all trans retinoic acid, 9-cis retinoic acid or 9-cis retinal may be used. Additionally analogues of retinoic acid may be used, for example 13-cis retinoic acid. The analogues can be different isomers that are functionally equivalent. Compounds that are metabolized to retinoic acid when administered are also considered analogues.

The utility of the present invention can be shown in the testing of new therapeutic approaches to prevent or control leiomyoma growth. For example, local application of potential therapeutic compounds on the leiomyomas can be undertaken via endoscopy. In one embodiment, the possible therapeutics can be applied in a pluronic gel. Possible therapeutic agents are antisense probes, antibodies (see Western blot protocols herein for specific antibodies) and drugs. The test compounds are administered and dosed in accordance with good pharmaceutical practice, taking into account the site and method of administration, scheduling of administration, body weight and other factors known to those in the art of drug testing.

For treatment of leiomyomas in mammals, such as humans and guinea pigs, the present invention provides for therapeutic agents which will control expression of the family of nuclear retinoic acid receptors (RAR, RXR, VDR, TR, PPAR). These agents are receptor selective agonists and antagonists of PPAR, RXR and the other members of the nuclear retinoic acid receptor family as are known in the art. The term agonist and antagonist or antagonizing is used in its broadest sense. The receptor selective compounds utilized in the present invention, are administered in combination with other drugs or singly consistent with good medical practice. The receptor selective agonists or antagonists are administered and dosed in accordance with good medical practice taking into account the clinical condition of the individual patient, the site and method of administration, scheduling of administration, and other factors known to medical practitioners. The "effective amount" for purposes herein is thus determined by such considerations as are known in the art and for each agonist or antagonist used. The amount must be effective to achieve improvement including but not limited to leiomyoma shrinkage, receptor expression downregulation and other indicators as are selected as appropriate measures by those skilled in the art.

The present invention also provides a method for monitoring the effectiveness of drugs to treat leiomyomas by monitoring the downregulation of PPAR-γ2 and RXRα expression taking into the account the menstrual cycle phase of the patient. Downregulation is associated with tumor shrinkage. In general a specimen of the leiomyoma is obtained through a biopsy procedure known to those skilled in the art. The tissue specimen can be assayed for expression levels by immunohistochemical and immunocytochemical staining (see generally Stites and Terr, *Basic and Clinical Immunology*, Appleton and Lange, 1994), ELISA, RIA, immunoblots, Western blotting, immunoprecipitation, and functional assays. mRNA complementary to the target nucleic acid sequence can be assayed by in situ hybridization, Northern blotting and reverse transcriptase—polymerase chain reaction. Nucleic acid sequences can be identified by in situ hybridization, Southern blotting, single strand conformational polymorphism, PCR amplification and DNA-chip analysis using specific primers as is known to those skilled in the art.

As shown in Example 1, the previous model of continuous $E_2$ exposure does produce small (1–3 mm diameter) leiomyomas on the uterine serosa, but usually along the blood supply line, and mainly on the anterior abdominal wall. In order to develop a model test system better resembling the anatomical location of human uterine leiomyomas, applicants developed a new model in which ovariectomized guinea pigs were exposed for at least one month to an estrogenic compound or analogues thereof and a retinoid compound or analogues thereof. In a preferred embodiment two $E_2$ implants and one implant containing all-trans retinoic acid (RA) or 9-cis-RA powder were used. RA by itself was antiestrogenic, as indicated by decreased size of the uterine horns; no tumors were produced with RA alone. The $E_2$+RA treatment caused a rapid regression (within two weeks) as seen by ultrasound of intra-abdominal wall leiomyomas but in the uterus, encapsulated, intramural and subserosal leiomyomas had formed. This mimics the clinical presentation of leiomyomas in women and is a significant, though unexpected, improvement of the model.

Small intra-abdominal wall tumors may appear after many months, presumably because the RA implant is (1) not delivering as well as the $E_2$ implant, (2) RA has been degraded, or (3) the animal has developed the enzymes needed to catabolize RA better than $E_2$.

Figure 1A:
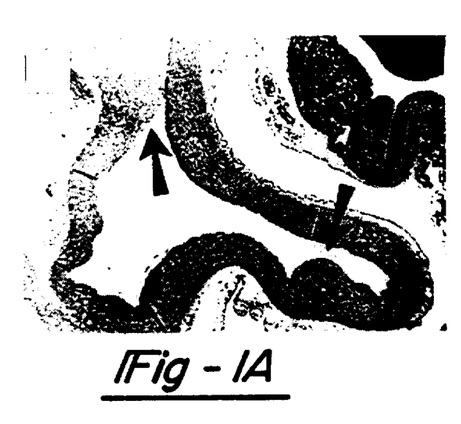
FIGS. 1A–F are photomicrographs of hematoxylin and eosin (H&E) stained 3 µm cross-sections of ascending aorta in guinea pigs treated for 8–9 months, wherein (A–C) shows intimal thickening (arrows) of the aorta seen in two young ovariectomized (OVX) animals treated with 17β-estradiol (E2) and all-trans retinoic acid (atRA) (B, C from one animal, original magnification: 4× A,B and 20× in C), (D) no thickening of the ascending aorta of a young OVX animal treated with E2 and 9-cis retinoic acid (9cRA) (4×), (E) intimal thickening of the aorta with focal calcifications in an old, non-OVX animal treated with E2 and atRA (4×), (F) intimal thickening of the aorta of an old, intact animal treated with E2 and 9-cis-retinaldehyde (10×)
Figure 1B:
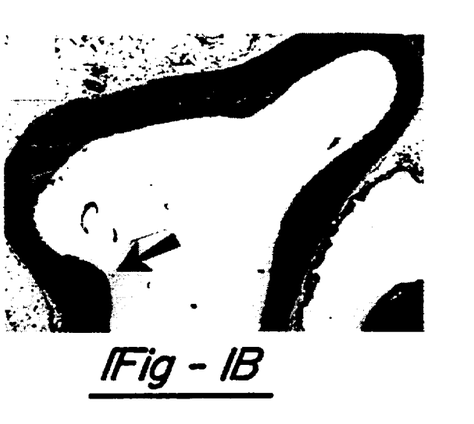
Figure 1C:
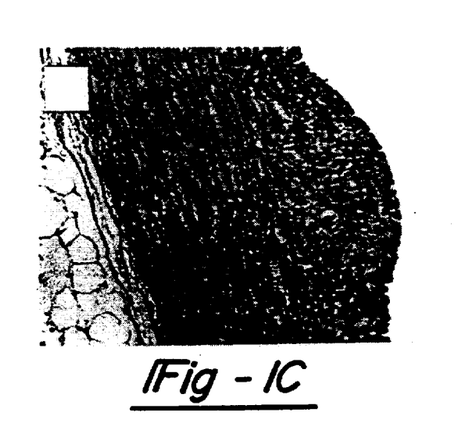
Figure 1D:
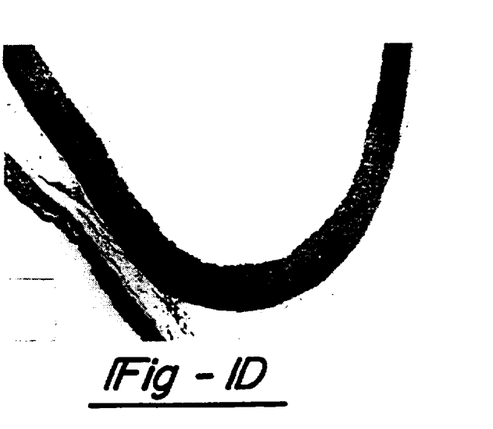
Figure 1E:
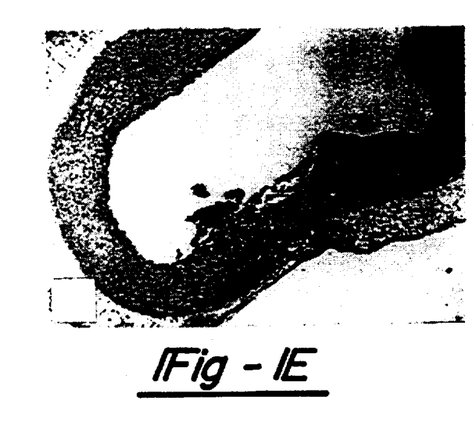
Figure 1F:
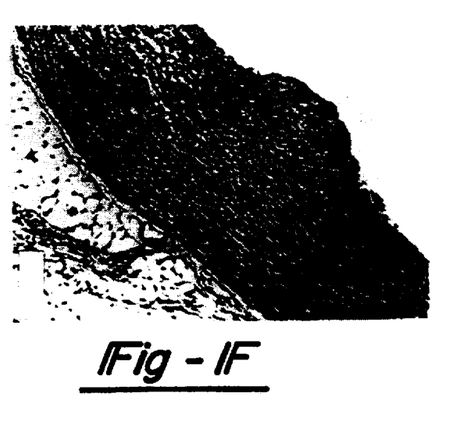
Figure 2A:
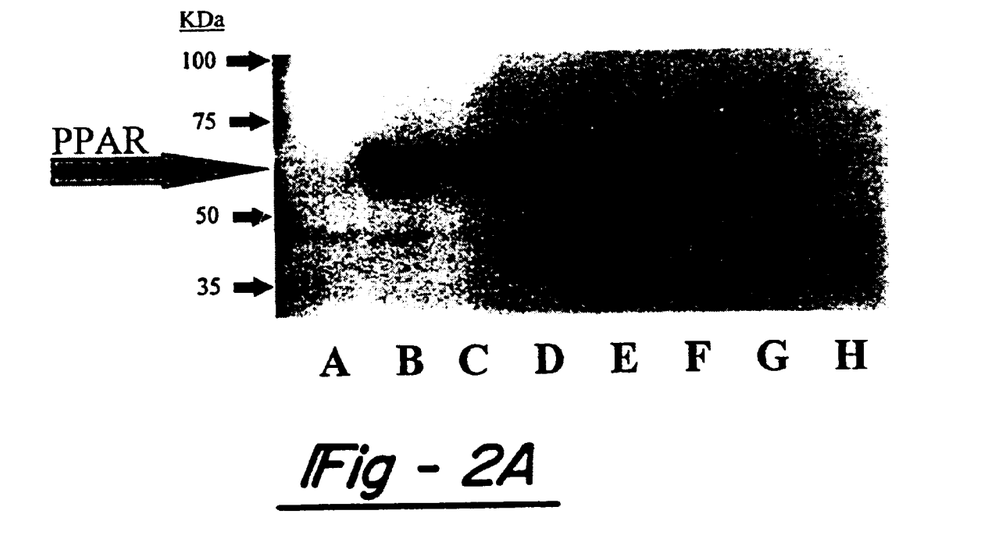
Figure 2B:
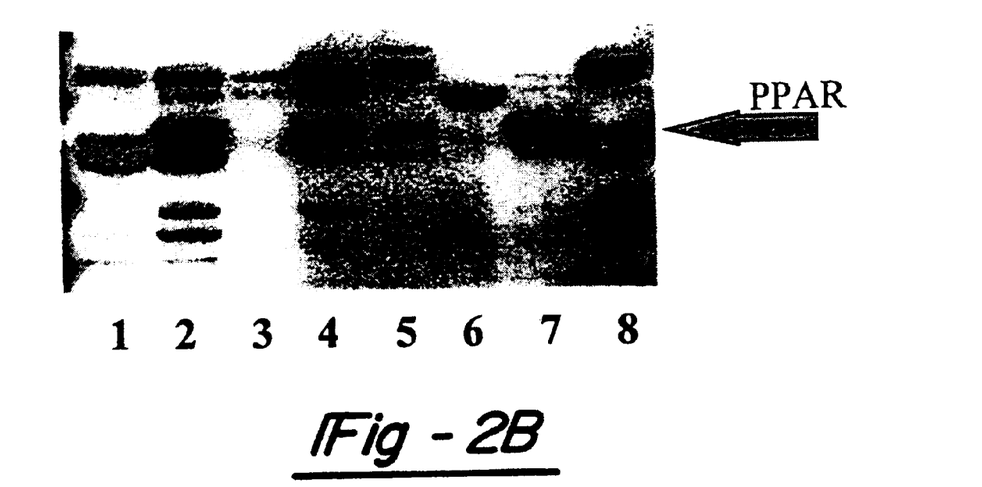

Western blots of uterine and leiomyoma extracts were studied which showed that, relative to $E_2$-treated only animals, the $E_2$+RA animals had higher protein levels of peroxisome proliferator-activated receptor (PPAR) (FIG. 2), than tumor-free uterine horns.

The present invention provides a model for testing of new therapeutic approaches during the initiation stage of atherosclerosis. Interestingly, there appear to be subtle variations in the type and dose of retinoid given with E2 that influence the formation of pre-atherosclerotic lesions, as seen in FIG. 2, and this emphasizes the versatility and usefulness of the model.

The H&E stained aorta cross-sections (FIG. 2) clearly indicate that intimal thickening occurred in animals treated with the same regiment (E2+RA) as required to develop uterine leiomyomas. Specifically, Panels a–c are obtained from two animals treated with E2+atRA for 306 days. Animals treated with empty implants showed no thickening and, surprisingly, one animal on 9-cis RA and E2 implants that developed uterine leiomyomas after 323 days showed also no thickening (Panel d). Different retinoids, i.e. atRA vs. 9-cis-RA, appear to show different efficiency in producing these pre-atherosclerotic lesions.

An older, OVX animal treated for 382 days with E2+atRA showed intimal thickening of the aorta with focal calcifications (Panel e); this animal developed uterine leiomyomas. Frequently, calcification is seen in leiomyomas from patients and from $E_2$+RA or $E_2$+9 cis RA-treated guinea pigs.

To test if these guinea pigs could metabolize the precursor 9-cis retinaldehyde (available from Sigma Chemical Co., St. Louis, Mo.) to 9-cis retinoic acid, the Applicants made a 9-cis retinaldehyde implant and placed it along with a E2 implant into an older but non-OVX animal. After 260 days, Applicants found intimal thickening (Panel f); however, this animal did not develop uterine leiomyomas. This observation allows the development of a model for atherosclerosis that is not coupled to uterine leiomyomas.

The above discussion provides a factual basis for the model of uterine leiomyomas and their use as a test system as well as the use of the model for early stage atherosclerosis. The methods used with and the utility of the present invention can be shown by the following non-limiting examples.

EXAMPLES

General Methods:

The terms follicular and proliferative or luteal and secretory phases of the menstrual cycle, respectively, are used interchangeably.

Implants: Each silastic implant (3×30 mm) was made with Dow Corning Co. (Midland, Mich.) medical grade silastic tubing (no. 602-305) and adhesive silicone (type A, no. 891) sealant and was filled with approximately 50 mg $E_2$ powder (Steraloids Inc., Wilton, N.H.); a 2-mm wooden plug separated the $E_2$ powder from the sealed end. For the RA implants, the all-trans retinoic acid (Sigma Chemical Co., Saint Louis, Mo.) or 9-cis retinoic acid (gift from Hoffman LaRoche, N.J.) were placed in the implant under dim light and stored under argon or helium until placed in the animal.

Animals: Dunkin-Hartley female guinea pigs were used. Young animals are defined as under one year and under 900 grams in weight. Older animals are defined as over two years old and generally at least 900 grams in weight.

Implantation: The implants were placed in the subcutaneous (s.c.) space of the intrascapular area either at the same time or seven to ten days after a bilateral oophorectomy or sham operation.

Light and Electron Microscopy and Immunocytochemistry: To evaluate the general morphology of the tumors (nodules) produced, tissues were fixed in 10% neutral buffered formalin and embedded in paraffin; 4-$\mu$m-thick sections were stained by hematoxylin-eosin and Masson trichrome (Luna, 1968). The cell phenotype of the tumors was studied by immunostaining for vimentin and desmin through use of the avidin-biotin complex (ABC) immunoperoxidase technique (Hsu et al., 1981). Mouse monoclonal antihuman vimentin antibody (Dako, Carpenteria, Calif.) and polyclonal antihuman desmin antibody, diluted 1:2 (Shandon-Lipshaw, Pittsburgh, Pa.) were used for demonstration of fibroblastic and SMC differentiation, respectively. Sections immunostained for desmin were trypsinized for two hours at 37° C. and microwaved for 20 minutes before final incubation for one hour at 37° C. Positive and negative (nonimmune serum) controls with hematoxylin-counterstained nuclei were included in all immunoreactions.

Representative tissues were fixed for electron microscopy in 2.5% glutaraldehyde in 0.1 M phosphate buffer (pH 7.2) and processed for electron microscopy in 2.5% glutaraldehyde in 0.1 M phosphate buffer (pH 7.2) and processed for ultrastructural evaluation of fibroblastic of SMC differentiation, as described previously (Nicosia et al., 1984).

Statistical Analysis: Fisher exact test, Wilcoxon's rank sum test (nonparametric), and t-test (parametric) were performed using the SAS program. Values in the text are mean±SEM.

Example 1

Estrogen-Only Induced Leiomyomas in Ovariectomized Guinea Pigs Prior Art Model

Specific Methods:

Serum $E_2$ and $P_4$: Serum $E_2$ was extracted with diethylether with 89% efficiency and was measured by an enzyme immunoassay (EIA) using the Boehringer-Mannheim (Indianapolis, Ind.) ES-300 analyzer. Intraassay and interassay coefficients of variance (CV) were 8.5 and 9.1%, respectively. Serum $P_4$ was extracted with 97% efficiency; intraassay and interassay CV were 13.3 and 22.4%, respectively.

Tissue $E_2$: Twenty to five hundred milligrams of a uterine serosal nodule, an abdominal wall tumor, or a cross section of a uterine horn with no visible signs of tumor were frozen with liquid nitrogen and pulverized. [6,7]-$^3$H-estradiol from DuPont (Boston, Mass.) was added to determine recovery. Tissue powders were extracted overnight with 5 ml absolute methanol (Glutek and Hobkirk, 1990) and then homogenized in the methanol suspension with a Duall homogenizer (Kontes Glass Co., Vineland, N.J.). The methanol was decanted, the pellets were further extracted with 5 ml diethylether, and the combined extracts were evaporated to dryness. $E_2$ levels were measured by EIA, and percentage recovery of radioactivity was 84.7±1.6 (mean±SEM; range 58–98, n=42).

Protocol:

Silastic $E_2$-implants were placed in 20 females divided in four groups: eight young non-ovariectomized (OVX), two young OVX, four older non-OVX, six older OVX. An additional four older OVX animals had empty (no $E_2$) implants for three months.

| Group No. | Age/Weight* | Animals | Oophorectomy | Estradiol |
|---|---|---|---|---|
| 1 | Young/460 | 8 | No | Yes |
| 2 | Young/483 | 2 | Yes | Yes |
| 3 | Old/927 | 4 | No | Yes |
| 4 | Old/925 | 6 | Yes | Yes |
| 5 | Old/935 | 4 | Yes | No |

*Average body weight (g) on the day estradiol implant inserted.

The results are summarized as follows:

1). Tumor development:

After three months on $E_2$, 8/8 OVX animals developed tumors which were benign smooth muscle tumors, i.e. leiomyomas (fibroids). As expected, none of the no-$E_2$ controls developed tumors.

Unexpectedly, only one out of 12 (8%) intact (non-OVX) animals developed tumors in the first three months. The tumor occurred on the abdominal wall in a young animal; that animal did not develop a tumor on the uterus. The difference in incidence of leiomyomas between OVX and non-OVX animals at three months was significant ($p<0.001$, Fischer exact test). The effect of ovariectomy on the production of tumors was independent of age ($p=0.67$ by the Fisher exact test).

The mode of $E_2$ delivery is important because Fujii (1981) found tumors in both OVX and non-OVX guinea pigs given $E_2$ benzoate intramuscularly three times a week for three months, whereas Lipschutz (1941) had used only OVX animals and either $E_2$ pellets or injections.

After six and nine months on $E_2$, 6/9 of the non-OVX animals did develop leiomyomas but they were not as numerous or large as in OVX animals. So the suspected ovarian "protection" from leiomyoma development is relatively brief.

2). Serum $E_2$ and $P_4$:

Until now there was no documentation in the literature on $E_2$ levels in guinea pigs with leiomyomas. Serum $E_2$, measured by EIA with the Boehringer Mannheim ES-300 analyzer and after extraction with ether, was 59.7.0±8.1 pg/ml (mean±SEM, n=9) in OVX and the days on the implant were 99.1±7.5 (mean±SEM; range 88–156 days). For non-OVX, serum $E_2$ was 132.8±34.7 (n=9) and days with the implant were 152.6±30.5 (range 83–311 days). There is no difference ($p>0.05$) in the serum $E_2$ levels between non-OVX and OVX animals. The non-OVX mean serum $E_2$ is twice that of term pregnancy serum $E_2$ of 59.3±8.9 pg/ml in guinea pigs (Batra et al, 1980).

Serum $P_4$, extracted with 97% efficiency, was less than 0.25 ng/ml in all $E_2$-implanted animals, as was expected since no corpora lutea were evident in the non-OVX $E_2$ animals. Non-pregnant and term pregnant serum $P_4$ is 3.6±0.7 and 102.0±3.3 pg/ml, respectively (Batra, et al, 1980). After six months one older animal developed ovarian cysts.

There was no correlation with serum $E_2$ and days on the implants; in two animals sampled twice there was a suggestion of a decline in the second $E_2$ value. Thus, two silastic implants, each 3×30 mm and containing 50 mg 17β-estradiol powder, are dispensing $E_2$ over 300 days and perhaps much longer.

3). Tissue $E_2$:

Serosal or abdominal leiomyomas and uterine horns (free of leiomyomas by gross observation and earlier histological evaluations) from $E_2$-treated animals were finely minced, extracted overnight with absolute methanol and then were mechanically homogenized with an all-glass Kontes homogenizer (Duall #22). The precipitated ground tissue was further extracted with diethylether. Percent $E_2$ recovery, determined in each sample with $^3$H-$E_2$ (Amersham), was 84.7±1.6) (n=42). $E_2$ levels (ng $E_2$/g wet tissue) were, respectively, 1.58±0.11 (mean±SEM) in non-leiomyoma uterine horns (n=17) and 1.69±0.22 (n=25) in the leiomyomas. No correlation between tissue $E_2$ and time on $E_2$-implant was observed but wide variation was seen in $E_2$ content of tumors of varying size from the same animal. It is doubtful that the leiomyomas make $E_2$, in the presence of exogenous $E_2$ from the implant, as suggested from increased aromatase mRNA levels in spontaneous human leiomyomas reported by Bulun at al.

4). Guinea pig body weights:

Animals were weighed on Monday and Friday as a measure of their well-being and to document differences in the growth rates of the various groups. To explain the putative "protective" effect of the ovaries applicants evaluated a number of parameters and found a difference ($p=0.04$ by repeated measures ANOVA of actual weights) in the relative changes in body weight of the OVX and non-OVX older groups which becomes apparent after 30–45 days of $E_2$ treatment. Dr. George N. Wade from the University of Massachusetts at Amherst, an authority on the effect of estrogens on metabolism (Wade), was contacted by the applicants and concurred that if serum $E_2$ in the non-OVX animals (see above) is indeed higher than in OVX a lower growth rate would be expected; $E_2$ is particularly effective in decreasing body fat content. Also, he agreed that it is unlikely that the weight of the leiomyomas in the OVX animals (estimated as 3%, at most) could account for the body weight differences.

5). Morphology:

All abdominal wall and uterine serosa nodules were characterized by spindly cells separated by a variable, usual small, amount of collagenous and microvascular stroma. No decidual cells were observed. Coexpression of desmin and vimentin was noted in almost all lesional spindle cells, supporting the smooth muscle nature of these cells. A minority of spindle cells exhibited only vimentin immunostaining and most likely represented fibroblasts. Similar cell morphology and immunostaining were noted in human leiomyomas.

Ultrastructural evaluation revealed that most of the spindle cells observed within the guinea pig nodules contained myofilaments and dense filamentous bodies, as well as frequent pinocytotic vesicles, as expected in typical SMCs. These cells were surrounded only partially by a basal lamina; their plasmalemmas displayed focal attachment plaques and occasionally contained profiles and cisternae of granular endoplasmic reticulum. Fewer lesional cells displayed exclusively the cytology of typical fibroblasts as indicated by free ribosomes and prominent granular endoplasmic reticulum. Extracellular collagen was present between all lesional cells.

Discussion of Example 1

A key factor in inducing SMC tumors (leiomyomas) in guinea pigs is the uninterrupted exposure to estrogen. In the original 1930's model, no differentiation was made between tumors consisting of fibroblasts and those consisting of smooth muscle. Lipschutz and Vargas (1939) had also induced tumors with subdermal $E_2$ pellets, and on the basis of applicants' findings, applicants suspect that these tumors were leiomyomas. In 1981, Fujii et al., studied the model and used electron microscopy after injecting $E_2$ benzoate three times a week for three months. They established that the tumors consisted of fibroblasts. An additional month of estrogen injections, combined with weekly low-dose $P_4$ injections, was necessary to change the composition of these tumors to smooth muscle and decidua cells.

The non-OVX group, which showed only an 8% incidence of tumors, had significantly higher $E_2$ levels, i.e., 140 pg/ml. This suggests that the removal of the ovaries is more important for leiomyoma formation than the maintenance of very high serum $E_2$. Another interpretation is that $E_2$ may have a bimodal effect, inducing leiomyomas at a lower level (attained in OVX animals) but decreasing their incidence at very high levels (as seen in non-OVX animals). Lower serum $E_2$ in OVX animals could be explained simply if these animals, having a more intense response to $E_2$ than non-OVX animals, had formed a thicker collagenous sheath around the implants, hindering the release of $E_2$; it was not possible to determine visually, however, whether a thicker collagenous sheath had been formed. In another study, (Yang et al., 1993), OVX rats treated with chronic $E_2$ implants also had lower serum $E_2$ levels than non-OVX rats, confirming our observations.

From descriptions of the model (Lipschutz and Iglesias, 1938; Lipschutz and Vargas, 1939; Lipschutz and Vargas, 1941; Lipschutz, 1942) it appears that larger tumors were produced with frequent injections of estrogens than by applicants' $E_2$ implants. Fujii et al. (1981) proposed that the tumors in their study resembled those observed in leiomyomatosis peritonealis disseminata (LPD), a rare human disease represented by the formation of numerous benign leiomyomas in submesothelial tissues. Uterine leiomyomas and LPD differ mostly by their anatomical location; histologically they are quite similar. Also, in this study, vaginal bleeding occurred in only two animals, whereas Lipschutz et al., (1938; 1939; 1941; 1942) and Nelson (1937) observed this routinely.

Negligible serum $P_4$ levels (below 0.025 ng/ml were found at three months of treatment and beyond. Had serum $P_4$ levels been high, this might have explained why non-OVX animals failed to develop leiomyomas early in treatment, since in previous studies (Fujii et al., 1981; Lipschutz et al., 1939) high doses of $P_4$ injected concomitantly with estrogen from the beginning prevented tumor formation.

Tissue $E_2$, expressed as nanograms per gram wet tissue, was measured in tumors and tumor-free uterine sections; it was expected that there would be differences between uterine leiomyomas, intra-abdominal wall leiomyomas, and normal tissues and a possible correlation with time of exposure to the $E_2$ implants. The data from the available specimens did not reveal such correlations. However, considerable, but not consistent differences in $E_2$ were found in tumors from different sites within an animal or among macroscopically tumor-free uterine samples.

Previous human leiomyoma studies by numerous investigators (for reviews see (Barbieri and Speroff, 1992; Tsibris and Spellacy, 1991)) showed that leiomyomas contain significantly higher $E_2$ and $P_4$ receptor levels than matched myometrium. Moreover, Bulun et al. (1994) reported that leiomyomas have three to four times higher aromatase activity and mRNA levels than myometrium.

The immunological and ultrastructural studies of this Example indicate that nodules produced by supraphysiological $E_2$ were leiomyomas. Lanari et al., (1990) gave a daily dose of diethlystilbestrol orally to younger OVX guinea pigs for three months and also produced peritoneal tumors composed of SMC and fibroblasts as determined by desmin and vimentin immunostaining. Unlike desmin, the intermediate filament vimentin is nonspecifically associated with mesenchymal cells and tumors, including SMCs and leiomyomas (Enzinger and Weiss, 1974), as also demonstrated herein.

In applicants' study, key features were the presence of myofilaments oriented parallel to the long axis cells, spindle-shaped densities or dense bodies, frequent pinocytotic vesicles, plasma membrane densities or attachment bodies, and poorly developed basal laminae. All such features have been described in normal human myometrium and human leiomyomas (Ferenczy and Richart, 1992). The occasional absence or scarcity of basal lamina material raises the possibility that some of the lesional cells within guinea pig nodules may represent activated myocytes or myofibroblasts (Schurch et al., 1992). However, it should be emphasized that the presence of a few myofibroblasts has been described in otherwise classical muscle cell tumors (Henderson et al., 1986) and perhaps indicates that there may be a continuum between fibroblasts and SMC, at least at the ultrastructural level.

Example 2

Estrogen and all-trans or 9-cis Retionic Acid Induced Leiomyomas

Methods:

Reagents: all trans retinoic acid was from Sigma Chemical CO., Saint Louis, Mo. and the 9-cis retinoic acid was a gift from Hoffman LaRoche, N.J.

(i) Tissue extraction:

Human myometrium, leiomyomas and guinea pig uteri and leiomyomas were extracted by the method of Furukawa et al. (1992). Briefly, 150 mg frozen tissue were cut in small pieces with a razor blade and placed in an Eppendorf tube containing one ml buffer consisting of 50 mM Tris-HCl pH 8, 120 mM NaCl, 0.5% Nonidet P-40, 100 mM NaF, 200 $\mu$M sodium ortho-vanadate, and 1 mg/100 ml each of aprotinin, phenylmethyl sulphonylfluoride and leupeptin. The tissues were dispersed with a Tekmar homogenizer for 15 seconds and after mixing end-over-end overnight at 4° C. the tubes were spun at 14,000 g for 45 minutes. The supernatants were used for the Western Blots. Protein content was estimated by the BCA (bicinchoninic acid) method using BSA as standard and 100 $\mu$g protein was used per lane. Novex 8% or 4–20% Tris-glycine gels (1 mm thick, 10-well) were used.

To extract glycoproteins, such as decorin which is related to TGFβs, some guinea pig tissues that had been previously homogenized in methanol and diethylether to extract $E_2$ and progesterone, were homogenized with a Tekmar homogenizer in a solution containing 4M guanidinium hydrochloride, 2 mM EDTA and 1 mM PMSF in 0.05 M sodium acetate pH 6.5. After an overnight mixing, as above, and centrifugation at 30,000 g for 30 minutes, the supernatants were exhaustively dialyzed (3.5 kDa cut-off) against water and lyophilized. The dry powders were dissolved in 0.05 M sodium acetate pH 6.5 at 6 mg/ml; samples are dispersed by brief sonication before aliquots of 80–100 μg are withdrawn for SDS-PAGE.

(ii) Antibodies:

Antibodies were gifts from other researchers or were purchased from commercial sources, as indicated. Bands were visualized with $^{125}$I-labeled Protein A from ICN and exposure to Kodak BioMax film. The alkaline phosphatase-tagged recombinant molecular weight markers were from Novagen.

Antibody to human receptor-α for 9-cis RA (RXR-α) was from Santa Cruz Biotechnology. Rat monoclonal antibody to an epitope between residues 89–105 of human vitamin D3 receptor was from Affinity Bioreagents, Inc. Antibody against a C-terminal human TGF-β3 epitope (residues 303–315) was from Santa Cruz Biotechnology. Antibody to recombinant full length (1–408) thyroid hormone receptor α1 (TRα1) of chicken origin was from Santa Cruz Biotechnology. Antibodies to TGFβ-receptor type I (α2733 specific for the IX-X-tail region) and type II (α2733 for the extracellular domain; α2617 for the VII/VIII kinase domain; α2616 for the IX/X/ tail in the kinase domain) were a gift from Dr. Xiao-Fang Wang. Antibodies raised against the C-terminal region (F-region) of human and mouse RA receptor γ were gifts from Dr. Pierre Chambon. Antibody was provided by Dr. Hector DeLuca to the hinge region of the Vitamin D3 receptor. Antibody raised against the full sequence (residues 1–454) of recombinant human RAR-γ and antibody raised against the N-terminus (residues 2–21) of the human RXR-α were from Santa Cruz Biotechnology. Antibody raised against an epitope at the C-terminal region (residues 484–498) of the peroxisome proliferator-activated receptor, PPAR, was from Affinity Bioreagents, Inc. Antibody raised against a C-terminus epitope (residues 430–447) of human RAR-β$_2$ was also from Santa Cruz Biotechnology.

(iii) Groups of animals and tissue samples compared by immunoblots:

$E_2$+RA animals: #19C, #23C and #113A.

19C-5, wedge of uterine horn, no tumor.

23C-A, uterine horn, no tumor; 23C-B, uterine leiomyoma.

113A-3, serosal leiomyoma; 113A-3A, cross section of uterine horn, no tumor; 113A-11, wedge from cervical and uterine body, no tumor.

$E_2$-only animals: AD$^{198}$, AG$^{79}$, AH2$^{79}$, AI$^{94}$, AK$^{244}$ (superscripts denote the days of exposure to two $E_2$ implants).

Extracts from abdominal (flat) leiomyomas, uterine serosal leiomyomas (blebs) and "whole" uterus (wedges of uterine horn, no tumor) were tested.

Results:

Comparison of the prior art model (Example 1) animals designated $E_2$ with the model of the present invention. Laparoscopy (see Example 4 for details on proceedure) was performed on all $E_2$+ all trans RA (n=15) and $E_2$+ 9-cis RA (n=5) guinea pigs. Two ovariectomized guinea pigs which were exposed to two $E_2$ and one RA implant for 275 days were laparoscoped and up to 7 mm in diameter uterine leiomyomas were seen. Smaller tumors can be produced in 30–90 days on $E_2$+RA. Serosal and intramural uterine leiomyomas are formed. The large intra-abdominal wall leiomyomas, seen in $E_2$-treated-only animals, were not present; occasionally, small intra-abdominal wall tumors were seen which were attributed to lengthy treatment, when the RA in the implant is no longer "active" or is delivered at a much decreased rate relative to that of $E_2$ or the animal increases its catabolism of RA thereby lowering its effective dose. The width of the cervix/uterine body was found to be much larger than that of the two horns. Treatment with retinoid compounds, such as RA or 9-cis Ra, but not $E_2$, produced no tumors; the horns and uterine body became very thin indicating that RA has an antiestrogenic effect. The treatment with RA-only produced silky hair on the animals.

In agreement with previously reported data from $E_2$-treated-only guinea pigs (Example 1; Porter, et al, 1995), the ovaries must also have a protective role in the RA+$E_2$ treated animals because intact animals on $E_2$+RA produce leiomyomas at a much slower rate, if at all, than ovariectomized animals.

H&E staining of the tumors, along with desmin immunostaining and electron microscopy, provided evidence that the observed tumors are leiomyomas.

When applicants used $E_2$+9-cis RA (a metabolite of all-trans RA, that binds RXRs with higher affinity than RARS), tumors similar in gross appearance were produced.

In a parallel experiment certain transcription regulator proteins were investigated that seemed relevant to leiomyoma formation, based on the production of leiomyomas in the guinea pig model of the present invention, to determine if they were overexpressed, downregulated or remained unchanged in leiomyomas, relative to normal (tumor-free) myometrium. Leiomyomas/uteri from the two guinea pig models ($E_2$ or $E_2$+RA) and human leiomyomas were analyzed to determine if they expressed a common "set" of these proteins.

Retinoic Acid Receptors (RARs) were tested for, since uninterrupted co-exposure of ovariectomized animals to all-trans RA and $E_2$ caused leiomyoma formation in an anatomically comparable fashion, as seen in women and as described herein above. Because of applicants' previous and current studies with human uterine leiomyomas and myometrium, applicants were able to compared human samples with animal uterine or intra-abdominal wall leiomyomas.

A technical note: Since all available antibodies were raised against man or rodent but not guinea pig protein sequences, applicants had to confine the comparison of expression levels within the two guinea pig treatments or within various human samples, but could not compare human with guinea pig samples.

Screening was undertaken for the following regulators of transcription:

1. Transforming growth factors (TGF) TGF-β3 and TGFβ receptor type II (TGFβ-RII)
2. RA receptors γ,
3. Retinoic acid receptor X α (RXR-α); RXR-α binds the 9-cis metabolite of all-trans RA,
4. Peroxisome proliferator-activated receptor (PPAR) which is a member of the superfamily of nuclear hormone receptors,
5. Vitamin D3 receptor (vit), and
6. Thyroid hormone receptor α1 (TRα1).

The Western Blot data did not show whether leiomyoma or tumor-free uterine horns or cervices contain higher or lower TGF-β3 levels. It is clear, however, that RA treatment in E$_2$-induced animals increased the level of TGF-β3 expression compared to E$_2$-treatment alone in the E$_2$ model.

For TGF-β receptor type II analysis two bands are observed at approximately 80 kDa and 60 kDa, the latter is probably an unglycosylated form rather than a degradation product. The TGFβ-RII levels in these samples did not follow the exact same pattern as TGF-β3, being highest in the horns and serosal leiomyoma but not the cervix of an animal (#113A) treated with E$_2$+RA. Very low TGFβ-RI levels are seen in the leiomyomas or uterine body of two E$_2$-only animals (AI and AH2).

Increased thyroid hormone receptor α1 (TRα1) may be important in leiomyoma production in the E$_2$-treated but not in the E$_2$+RA animals. Specifically, the strongest bands for TRα1 were seen are two abdominal wall leiomyomas (animals AI and AH2), whereas the uterine body/cervix of animal AI shows no TRα1. Among the E$_2$+RA samples, TRα1 is highest in the uterine horn but not in a serosal leiomyoma or the enlarged cervix. The TRα1 antibody applicants used was made against the full-length recombinant TRα1; other commercially available peptide-specific antibodies to TRα1 would probably not have detected it in these samples. Four TRα1 bands were detected with this antibody in human uterine extracts.

RAR-γ was probed with three antibodies. The antibody from Santa Cruz, which was made to the full-length recombinant RAR-γ, detected RAR-γ in all guinea pig samples. In the E$_2$+RA and E$_2$-treated animals similar RAR-γ levels were observed. A comparison of tissue from E$_2$-treated animals showed that RAR-γ levels were declining the longer the animals were exposed to the E$_2$ implants (79, 198 and 244 days).

The RXR-α Western blots were very revealing in that two RXRα bands were seen in the tumor-free uterine horns but none in the tumor-free cervical section or serosal tumors. The implication is that RXRα is not expressed in the leiomyoma thus allowing the tumors to grow.

PPAR protein levels are higher in the E$_2$+RA compared to the E$_2$-only samples; longer film exposure revealed that in E$_2$ animals PPAR appears as a doublet and is elevated in the two intra-abdominal wall leiomyomas relative to the serosal leiomyoma (See further Example 3).

Data from representative human uterine samples was obtained at different hormonal "conditions". Specifically, matched pairs of leiomyomas (L) and tumor-free myometria (M) were selected from patients undergoing hysterectomy at the proliferative (follicular), secretory (luteal) phases of the menstrual cycle, after menopause (PM) or after three-month therapy with a GnRH agonist (Leupron) which caused severe hypoestrogenism and leiomyoma regression.

In all blots applicants detected the corresponding antigens (i.e. TGFβs or receptors) with the predicted size(s). Immunostaining of human leiomyoma (L) and matched myometrial (M) extracts was undertaken with the TGF-β3, TGFβ-RI, TGFβ-RII, RAR-γ, PPAR and TRα1 antibodies, antibody raised against a C-terminus epitope (residues 430–447) of human RAR-β2 antibodies, antibody raised against an N-terminus epitope (residues 2–21) of human receptor-α for 9-cis RA (RXR-α), rat monoclonal antibody to an epitope between residues 89–105 of human vitamin D3 receptor. The intensity of the L and M bands among the four groups of patients were remarkably similar. The Leupron patient showed the highest expression of TGF-β3, TGFβ-RI, TGFβ-RII, RAR-γ, RAR-β, RXR-α, TRα1 and vitamin D3 receptor than patients in the secretory phase or after menopause. The Leupron tumors are the current "standard" of regressing leiomyomas. They provide a comparison/control for evaluating other anti-leiomyoma drugs in the model of the present invention. The leiomyoma from the proliferative phase patient, where we hypothesize these leiomyomas grow, appears to express higher levels of these proteins than the adjacent tumor-free myometrium.

The above data herein shows the usefulness of present invention of an in vivo model for leiomyoma. The present invention because of its close resemblance to the human condition can be used in the design and testing of new drugs (see for example Porter et al., 1996 for an example of such a study using the prior art model). Cell cultures while useful for clarifying details about reaction mechanisms do not adequately address the use of drugs in the whole organism because all the "environmental cues" are missing.

In summary, if given alone, atRA or 9-cisRA had no toxic effect and the body weight increased (as opposed to E2 which causes a gradual weight loss); also, their hair became thick and silky. By palpation, the RA+E2 animals had no abdominal tumors but laparotomy revealed encapsulated uterine tumors but no abdominal tumors. These, and the 9-cisRA-induced-tumors, were leiomyomas by H&E, immunostaining and electron microscopy; data are not shown but are identical to human leiomyomas or guinea pig abdominal leiomyomas, as documented previously (Porter, 1995). Immunostaining showed strong and diffuse cytoplasmic expression of desmin. Electron microscopy, the definitive method to prove that these are smooth muscle cells, showed characteristic spindle morphology of smooth muscle cells (×7,300 magnification) and numerous filaments focally aggregated into dense bodies, with pinocytotic vesicles evident below the plasma membrane (×76,000).

Cervical polyps: It was quite intriguing to find large cervical tumors in 4/9 of animals treated with two E2 and one atRA implant. These tumors were shown by H&E staining to be benign squamous papillomas (fibroepithelial polyps). None of the five E2+9-cisRA or E2-only animals ever developed such tumors.

There are two main conclusions from our data to date:

1) Intact (non-ovariectomized—OVX) animals do not develop tumors, except very late, revealing again that the ovaries during chronic E2+RA stimulation offer an apparent protection from tumor formation.

2) Leiomyomas are well tolerated by OVX animals on E2+RA, for as long as they have been tested (400 days).

By comparison, in E2-only animals larger and more numerous tumors are formed (mainly on the abdominal wall and serosal bowel) by 90–120 days; after 200 days, the tumor burden becomes too large with the possibility of bowel obstruction necessitating the termination of the experiment. Thus, when the tumors are confined to the uterus they are not life-threatening, as is the case in most women.

Example 3

Further Study of PPAR and RXR-α

During Applicants' study of various genes expressed in leiomyomata as set forth in Example 2, Applicants used a commercially available antibody for PPAR-γ2 (Peroxisome Proliferation Activated Receptors, subtype gamma). Applicant now has available from Dr. Bruce Spiegelman's Lab (Dana Farber Cancer Institute) a second antibody for PPAR-γ2 and has undertaken further study of PPAR. Improved Western Blots (immunoblots) relative to the data with a commercial antibody (Example 2) were obtained.

Reagents/Methods:

Western Blots: Precast Novex NuPAGE gels (4–12%, 1 mm thick) and SDS-βME are used in MOPS buffer. Generally, 100 μg protein per well is applied and the gels run at 200 V for 50 min. Molecular weight markers, recombinant tagged with S-tag, from Novagen (Madison, Wis.) are used. After transfer to a nitrocellulose membrane for 30 minutes at 25 V, the gels are blocked in buffer which contains $Na_2HPO_4$/1% casein/NaCl and 0.02% thimerisol, as preservative. Then, the appropriate amount of primary antibody is added for 1–2 hours or overnight, followed by the appropriate secondary antibody and antibody to S-tag. In this example bands were visualized using a chemiluminescence kit from Amerscham Co.) and exposure to Kodak or Amersham film. The recombinant molecular weight markers conjugated to horseradish peroxidase were from Novagen.

The data show that

1. Human leiomyomata overexpress the PPAR nuclear receptor protein some 5-fold, on the average (n=7), than matched myometrium (FIG. 2A).
2. This PPAR-γ2 overexpression is seen only in uteri removed from the patient at the proliferative phase of her menstrual cycle, but not in uteri from the secretory phase (data not shown).
3. Using similar guinea pig uterine extracts, Applicants obtained comparable results to those from human leiomyomata (FIG. 2B).

Specifically, uterine serosal leiomyomata showed a 3-fold increase of PPAR-γ2 protein expression relative to the tumor-free uterine horn. Leiomyomata on the abdominal wall (the main site of tumor development in animals treated only with estrogen) showed much lower levels of PPAR-γ2 protein than uterine leiomyomata.

In a similar experiment, the Applicants tested by Western blots the expression of the retinoic X receptor α (RXR-α) protein, as done for FIG. 2, and found that the RXR-α molecular mass approximately 50 KDa) was also overexpressed in human leiomyoma extracts relative to myometrial extracts from the same uteri; again, the proliferative phase uteri showed RXR-α expression but not the secretory phase uteri, as seen with PPAR-γ2 (FIG. 2).

A hypothesis for the above observations can be made, but it is not to be construed as limiting the present invention to this one mode of action. Leiomyomata overexpress PPAR-γ2 AND RXR-α, which are not only just another members of the nuclear receptor superfamily consisting of retinoic acid receptors among others, but dimerizes with them to regulate gene expression. PPAR-γ2 is mainly expressed in adipocytes (fat cells) and is considered a marker for adipocytes (albeit not with absolute specificity).

The menstrual cycle phase-dependent expression of PPAR-γ2, namely, in the estrogen-dominated phase of the cycle implies that estrogen is the likely dominant regulator of tumor development.

The results confirm (FIG. 1, lanes 3, 6 and 8) that the addition of retinoic acids in the model produces leiomyomata that not only look like the human ones by their anatomical (uterine) location and morphology, but also show expression of common genes, like PPAR-γ2 (FIG. 1, lanes 2, 4 and 7), as in humans, OEDs, therefore the model is appropriate for human studies. This is the first evidence that abdominal wall and uterine wall tumors are different.

Further, these results demonstrate that the effectiveness of drugs to treat leiomyomas can be evaluated by monitoring PPAR-γ2 and RXRα expression as well as other members of the receptor superfamily. Currently, as with the use of Leupron, success in treating leiomyomas is ascertained by observing shrinkage of the leiomyomas. The monitoring of PPAR and RXRα expression, and expression of other members of this receptor family, can be done via a tissue biopsy before shrinkage is apparent. This allows early evaluation both in humans and animals being treated with a drug.

The observation of the overexpression of PPAR and RXR-α in leiomyomas indicates that the involvement of these members of the nuclear receptor superfamily (those that function as hetero-dimers, e.g. PPARγ2-RXRα) is central to the etiology and growth regulation of uterine leiomyomas and can be useful in developing new therapeutic modalities for abnormal growth of smooth muscle cells in the uterus and the vascular system.

Note that occasionally, small intra-abdominal wall tumors were seen in animals which are attributed to lengthy treatment, when the RA in the implant is no longer as "active" or is delivered at a much decreased rate relative to that of $E_2$ or the animal increases its catabolism of RA thereby lowering its effective dose. Two classes of intracellular retinoid-binding proteins exist, CRBP (cellular retinol-binding protein I and II) and CRABP (retinoic acid-binding proteins I and II) (Donovan, Napoli). They bind retinoids with a Kd of 0.1–1 nM and will control the availability of RAs to the RA receptors. A rapid isomerization of atRA and 9-cisRA occurs and will also influence their availability the RA receptors (Kojima et al., 1994). From numerous human studies it is known that retinoid resistance develops which would lead to a progressive decrease in plasma RAS even if the implants used in the present model maintained a constant delivery of RAs.

Example 4

Development of Endoscopic and Ultrasound Techniques in the Guinea Pig Leiomyoma Model Dunkin Hartley guinea pigs, body weight ranging from 500–1300 g, were evaluated.

Laparotomy and endoscopy were performed under anesthesia via intramuscular injection of 0.2 mL atropine and 1 mL per kg of a 7:3 mixture, respectively, of ketamine HCl (100 mg/mL) and xylazine (20 mg/mL). Oophorectomies were performed via laparotomy; hemoclips were placed across the ovarian ligament and the mesoovarium. Leiomyomata were followed by ultrasonography (Ultramark 4+, ATL, Bothington, Wash.). Tumor dimensions, length and depth, in transverse and sagittal views were measured with calipers on stored sonographic images. The dimensions of the cervix, uterine body and horns were also recorded.

After abdominal wall and uterine leiomyoma formation was noted by ultrasound, the guinea pigs underwent endoscopy via a 1.9 mm zero degree diagnostic endoscope (Karl Storz, Culver City, Calif.) under anesthesia, as described above. The bladder was continuously drained via a 2.4 mm urethral catheter (Baxter Healthcare Co., Valencia, Calif.). The abdomen was shaved, cleaned with betadine and draped in a sterile fashion. A 3 mm transverse midline supraumbilical incision was made with a number 11 blade. After penetrating the skin, a sharp 2 mm trocar and sheath (KarlStorz, Culver City, Calif.) were placed in the peritoneal cavity. After removal of the trocar from the sheath, the optical catheter was inserted and connected to the xenon light source. Once the peritoneal cavity entry was confirmed, a pneumoperitoneum was initiated. The peritoneal cavity was insufflated with a hysteroscopic $CO_2$ insufflator (KarlStorz, Culver City, Calif.) at 15 mL/minute. The initial intraabdominal pressure upon entry was 3–5 mm Hg and was maintained below 7 mm Hg. Accessory ports were established above the pubic symphysis under direct visualization. Skin staples (PGX-35W; 3M, St. Paul, Minn.) were used for routine skin closure.

Uterine horn images were occasionally obscured by an empty bladder or bowel gas shadows. Discrete shadowing, as seen in humans, was also found in guinea pig leiomyomata. No cardio-pulmonary complications were incurred in the animals with the pneumoperitoneum. Endoscopy has been repeated on the same animals three times, over a four month period, with no added complications.

In animal models the development of non-invasive or less invasive techniques than laparotomy, reduces stress that may compromise chronic experiments as described herein. The introduction of high frequency transducers with short field resolution (the focal length of the 10 MHz probe is 2 cm and its axial resolution 0.4 mm) allow visualization of superficial structures, such as abdominal leiomyomata, and frequent monitoring of leiomyoma growth and regression. The results are reassuring since serial follow up of leiomyomata with ultrasound was reliable. The development of endoscopic techniques allowed confirmation of the ultrasound results in a prospective manner along with the availability of tissue sampling. Currently, ultrasonography is used to determine optimal intervals for endoscopic verification of tumor size and laparotomy.

These techniques allow not only optimal timing of interventions but reduce the number of animals required by allowing paired observations rather than requiring the larger group sizes necessary to determine significant differences in group means.

Laparoscopic techniques require a pneumoperitoneum while maintaining low intraabdominal pressure with the use of a hysteroscopic insufflator. Carbon dioxide was used since its refractive index is the same as air and provided optimal viewing clarity and is absorbed rapidly.

In the guinea pig model, monitoring of uterine and leiomyoma size can be quantitated by ultrasonography and endoscopy. These techniques in addition to the monitoring of PPAR expression allows accurate determination of drug responses in the model of the present invention.

Throughout this application, various publications, are referenced by citation. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Allegretto et al., "Transactivation properties of retinoic acid and retinoid X receptors in mammalian cells and yeast. Correlation with hormone binding and effects of metabolism" J Biolog Chem 268:26625 (1993).

Barbieri, ed. Leiomyoma utero in Seminars in reproductive endrocinology 10:301–390 (1992).

Batra, et al., "Sex steroids in plasma and reproductive tissues of the female guinea pig" Biol. Reprod. 22:430–437 (1980).

Breslow, "Mouse models of atherosclerosis" Science 272:685–688, 1996.

Bulun et al., "Expression of the CYP19 gene and its product aromatase cytochrome P450 in human uterine leiomyoma tissues and cells in culture" J Clin Endocrinol & Metab, 78:736–743 (1994).

Carlson et al., "Indications for hysterectomy" New Engl J Med, 328:856–860 (1993).

Enzinger et al., in Soft Tissue Tumors, 2nd ed., St. Louis: Mosby, p. 89 (1988).

Everitt, et al., "Rodent model of reproductive tract leiomyomata. Clinical and pathology features" Amer J Pathol 146:1556 (1995).

Fekete, "Animal models in experimental atherosclerosis: a critical review" Acta Veterinaria Hungarica 41:3–9 (1993).

Ferenzy and Richart, in Female reproductive system: dynamics of scan and transmission electron microscopy, New York: Wiley and Sons, pp. 197–207 (1974).

Field et al., "Spontaneous reproductive tract leiomyomas in aged guinea-pigs" J Comp Pathol, 101:287–294 (1989).

Finkelman et al., "Ovariectomy selectively reduces the concentration of transforming growth factor (in rat bone: implications for estrogen deficiency-associated bone loss" Proc Natl Acad Sci USA, 89:12190–12193 (1992).

Fotis et al., "The endogenous oestrogen metabolite 2-methoxyoestradiol inhibits angiogenesis and suppresses tumor growth" Nature, 368:237–239 (1994).

Friedman and Barbieri: "Leuprolide acetate". Applications in gynecology. Curr Probl Obstet Gynecol Fertil 11:205 (1988).

Fujii et al., "Progesterone-induced smooth muscle-like cells in the subperitoneal nodules produced by estrogen. Experimental approach to leiomyomatosis peritonealis disseminata". Am J Obstet Gynecol 139:164–172 (1981).

Furukawa et al., J. Biol. Chem. 267:17121–17127 (1992).

Glutek and Hobkirk, "Estrogen sulfatase and steroid sulfatase activities in intrauterine tissues of the pregnant guinea pig" J Steroid Biochem Mol Biol, 37:707–715 (1990).

Harkness and Wagner, in The Biology of Rabbits and Rodents, 3rd ed. Philadephia: Lea Sebiger Publisher; p. 21 (1989).

Henderson et al., in Ultrastructural appearance of tumours, 2nd ed., Edinburgh: Churchill Livingstone, p. 231 (1986).

Howe et al., "Rodent model of reproductive tract leiomyomata. Establishment and characterization of tumor-derived cell lines" Amer J Pathol 146:1568 (1995).

Hsu et al., "The use of avidin-biotin-peroxidase techniques" J Histochem Cytochem, 29:577–580 (1981).

Kiechle-Schwarz et al., Nonrandom cytogenetic changes in leiomyomas of the female genitourinary tract. A report of 35 cases. Cancer Genet Cytogenet 53:125 (1991).

Kjerulff et al., Hysterectomy and race. Obstet Gynecol 82:757 (1993).

Kojima et al., "In vivo isomerization of retinoic acids. Rapid isomer exchange and gene expression" J Biol Chem 269:327000 (1994).

Lanari et al., "Progesterone receptors in estrogen-induced fibromatosis of guinea pigs" Cancer Lett, 51:235–245 (1990).

Larner et al., "The isolation and characterization of estradiol-fatty acid esters in human ovarian follicular fluid" J Biol Chem, 268:13893–13899 (1993).

Lipschutz, "Experimental fibroids and the antifibromatogenic action of steroid hormones" J Am Med Assoc, 120:171–175 (1942).

Lipschutz and Iglesias, "Multiples tumeurs uterines et extragenitales provoquees par le benzoate d'oestradiol" C F Soc Biol Paris, 129:519–528 (1938).

Lipschutz and Vargas, "Experimental tumorigenesis with subcutaneous tablets of oestradiol" Lancet, 1:1313–1318 (1939).

Lipschutz and Vargas, "Structure and origin of uterine and extragenital fibroids induced experimentally in the guinea pig by prolonged administration of estrogens" Cancer Res 1:236–249 (1941).

Lipschutz et al., "Antitumorigenic action of progesterone" Lancet 1:420–421 (1939).

Lipschutz et al., "Dose hysterotrophe "utile" et dose "tumorigene" de l'oestradiol et de l'oestrone libres" C R Soc Biol, 130:939–942 (1939a).

Lumsden, et al., "The binding of steroids to myometrium and leiomyomata (fibroids) in women treated with the gonadotrophin-releasing hormone agonist Zoladex (ICI 118630)" J Endocrinol 121:389 (1989).

Luna, in *Manual of Histologic Staining Methods of the Armed Forces* Institute of Pathology, 3rd ed., New York: McGraw-Hill, 38–39 and 94 (1968).

Mangelsdorf and Evans, "The RXR heterodimers and orphan receptors" Cell;83:841 (1995).

Mangelsdorf et al., "Overview: The nuclear receptor superfamily: The second decade" Cell 83:835 (1995).

Nagpal et al., "Separation of transactivation and AP1 antagonism functions of retinoic acid receptor $\alpha$" J Biolog Chem 270:923 (1995).

Nelson, "Endometrial and myometrial changes, including fibromyomatous nodules, induced in the uterus of the guinea pig by the prolonged administration of oestrogenic hormone" Anat Rec, 68:99–102 (1937).

Nicosia et al., "Isolation and ultrastructure of rabbit ovarian mesothelium (surface epithelium)" Int J Gynecol Pathol, 3:348–360 (1984).

Paigen et al., "The mouse as a model for human cardiovascular disease and hyperlipedimia" Current Opinion in Lipidology 5:258–264, 1994.

Pandis, et al., "High resolution mapping of considtent leiomyoma breakpoints in chromosomes 12 and 14 to 12q15 and 14q24.1" Genes Chrom Cancer 2:227 (1990).

Porter et al., "Ovariectomized guinea pigs with silastic 17β-estradiol implants: How good a model for leiomyomas? Biol Reprod, 48(suppl 1):89 (abstract 124) (1993).

Porter et al., "Estrogen-induced guinea pig model for leiomyomas: Do the ovaries protect?" Biol. Reprod. 52:824–832 (1995).

Porter et al., "Raloxifene Causes Rapid Regression of Abdominal Wall Leiomyomas in the Estrogen-Induced Guinea Pig Model" *J Soc Gynecol Invest*, Vol. 3, No. 2 (Supplement) (1996)

Rein, et al., "Cytogenetic abnormalities in uterine leiomyomata" Obstet Gynecol 77:923 (1991).

Rein and Nowak, "Biology of uterine myomas and myometrium in vivo" Semin Reprod Endocrinol, 10:310–319 (1992).

Rogers and Blumenthal, "Studies of guinea pig tumors. I. Report of 14 guines pig tumors, with a review of the literature" Cancer Res, 20:191–197 (1960).

Romagnolo et al., "Estradiol-dependent uterine leiomyomas in transgenic mice" J Clin Invest 98:777–784 (1996).

Sadan et al., "Oestrogen and progesterone receptor concentration in leiomyoma and normal myometrium" Ann Clin Biochem 24:263 (1987).

Savouret et al., "Interplay between estrogens, progestins, retinoic acid and AP-1 on a single regulatory site in the progesterone receptor gene" J Biol Chem 269:28955 (1994).

Schoen, "Blood Vessels", In Pathologic basis of disease, R. S. Cotran, V. Kumar and S. L. Robbins (editors), 5th ed., W. B. Saunders Co., Philadelphia, Pa., 1994, pp. 467–516.

Schurch et al., in Sternberg SS (ed.), Histology for Pathologists. New York: Raven Press, pp. 109–144 (1992).

Senekjian et al., "Comparison of the quantity of estrogen receptors in human endometrium and myometrium by steroid-binding assay and enzyme immunoassay based on monoclonal antibodies to human estrophilin" Am J Obstet Gynecol 160:592 (1989).

Simionescu and Simionescu, "Preatherosclerotic events: pathoiochemical changes occuring in the arterial wall before monocyte migration" FASEB J 7:1359–1366 (1993). Stewart and Friedman, "Steroidal treatment of myomas: preoperative and long-term medical therapy" Semin Reprod Endocrinol, 10:344–357 (1992).

Tsibris and Spellacy, "Potential regulation of uterine leiomyomas by epidermal growth factor, platelet-derived growth factor, IGF-I, insulin and steroids", In The Extracellular Matrix and the Reproductive Tract, PC Leppert and J F Woessner Jr, eds, Perinatology Press, Ithaca N.Y., pp 224–234 (1991).

Tsibris et al., "Estrogens and protein disulfide isomerase systems", Tn The New Biology of Steroid Hormones. R. B. Hochberg, and F. Naftolin, editors. Serono Symposia vol. 74, Raven Press, NY. 235–249 (1991a).

Tsibris et al., "Retinoic Acid Involvement in Leiomyoma Development: An Animal Model" *J Soc Gynecol Invest*, Vol. 3, No. 2 (Supplement) (1996).

Wilcox et al., "Hysterectomy in the United States, 1988–1990" Obstet Gynecol., 83:549–555 (1994).

Yang et al., "Effects of long-term estradiol exposure on the hypothalamic neuron number" Acta Endocrinol, 129: 543–547 (1993).

What is claimed is:

1. A method of making a guinea pig model for uterine leiomyoma comprising a) ovariectomizing a young female guinea pig; and b) delivering an estrogenic compound or a functionally active equivalent thereof and a retinoid compound or a functionally active equivalent thereof such that the guinea pig develops uterine leiomyoma.

2. A method of making a guinea pig model for uterine leiomyoma as set forth in claim 1 wherein the estrogenic compound or functionally active equivalent thereof and the retinoid compound or functionally active equivalent thereof are delivered using silastic implants.

3. A method of making a guinea pig model for uterine leiomyoma as set forth in claim 2 wherein the estrogenic compound or functionally active equivalent thereof is delivered using two silastic implants and the retinoid compound or functionally active equivalent thereof is delivered using at least one silastic implant.

4. A method of making a guinea pig model for uterine leiomyoma as set forth in claim 1 wherein the retinoid compound or a functionally active equivalent thereof is selected from the group consisting of all-trans retinoic acid, 9-cis retinoic acid, 9-cis retinal.

5. A method of making a guinea pig model for uterine leiomyoma as set forth in claim 1 wherein said estrogenic compound is selected from the group consisting of estradiol-17β ($E_2$), $E_2$-metabolites, estron, 17-esters of $E_2$, 2-methoxyestradiol, catecholestrogens, and synthetic estrogens.

6. A guinea pig model for uterine leiomyoma made by any of the methods of 1–5, wherein the guinea pig develops uterine leiomyoma.

* * * * *